(12) United States Patent
Dunne

(10) Patent No.: US 10,471,209 B2
(45) Date of Patent: Nov. 12, 2019

(54) AUTO-INJECTOR ASSEMBLY

(71) Applicant: New Injection Systems Ltd, Ipswich Suffolk (GB)

(72) Inventor: Stephen Dunne, Ipswich Suffolk (GB)

(73) Assignee: NEW INJECTION SYSTEMS LTD., Ipswich, Suffolk (GB)

( * ) Notice: Subject to any disclaimer, the term of this patent is extended or adjusted under 35 U.S.C. 154(b) by 335 days.

(21) Appl. No.: 14/646,911

(22) PCT Filed: Nov. 25, 2013

(86) PCT No.: PCT/EP2013/074647
§ 371 (c)(1),
(2) Date: May 22, 2015

(87) PCT Pub. No.: WO2014/080020
PCT Pub. Date: May 30, 2014

(65) Prior Publication Data
US 2015/0320936 A1 Nov. 12, 2015

(30) Foreign Application Priority Data

Nov. 23, 2012 (GB) .................................. 1221086.0
Dec. 13, 2012 (GB) .................................. 1222426.7
(Continued)

(51) Int. Cl.
*A61M 5/31* (2006.01)
*A61M 5/28* (2006.01)
(Continued)

(52) U.S. Cl.
CPC ............ *A61M 5/31* (2013.01); *A61M 5/2033* (2013.01); *A61M 5/286* (2013.01); *A61M 5/288* (2013.01);
(Continued)

(58) Field of Classification Search
CPC ...... A61M 5/31; A61M 5/2033; A61M 5/286; A61M 5/288; A61M 5/3202;
(Continued)

(56) References Cited

U.S. PATENT DOCUMENTS 906,574 A  12/1908 Stebbins
2,871,856 A  2/1959 Steiner
(Continued)

FOREIGN PATENT DOCUMENTS

CN  102316918 A  1/2012
DE  19622124 A1  12/1997
(Continued)

OTHER PUBLICATIONS

PCT International Search Report and Written Opinion dated Feb. 26, 2014 for PCT/EP2013/074084 filed Nov. 18, 2013, 10 pgs.
(Continued)

*Primary Examiner* — Lauren P Farrar
(74) *Attorney, Agent, or Firm* — Fredrikson & Byron, P.A.

(57) ABSTRACT

An auto-injector assembly comprises a medicament container defining a substantially cylindrical chamber containing a liquid medicament. A proximal end of the chamber is closed by a piston and a distal end of the chamber is closed by a seal spanning an opening. A biasing means, such as a spring, is coupled to the piston and acts to bias the piston towards the seal, thereby pressurizing the liquid medicament. The assembly also comprises a hypodermic needle and a removable needle cap for maintaining the hypodermic needle in sterile conditions until use. A means for establishes fluid communication between the chamber and the hypodermic needle such that the pressurized liquid medicament is automatically delivered through the hypodermic needle when communication has been established.

20 Claims, 9 Drawing Sheets

(30) Foreign Application Priority Data

| | | |
|---|---|---|
| Mar. 12, 2013 | (GB) | 1304392.2 |
| Apr. 4, 2013 | (GB) | 1306062.9 |
| Apr. 9, 2013 | (GB) | 1306382.1 |

(51) Int. Cl.
  *B65B 3/00* (2006.01)
  *B65B 7/16* (2006.01)
  *A61M 5/20* (2006.01)
  *A61M 5/32* (2006.01)

(52) U.S. Cl.
  CPC .............. *B65B 3/003* (2013.01); *B65B 7/161* (2013.01); *A61M 5/3202* (2013.01); *A61M 2005/3121* (2013.01); *A61M 2207/00* (2013.01)

(58) Field of Classification Search
  CPC ...... A61M 2005/3121; A61M 2207/00; B65B 3/003; B65B 7/161
  See application file for complete search history.

(56) References Cited

U.S. PATENT DOCUMENTS

| | | | |
|---|---|---|---|
| 3,207,157 | A | 9/1965 | Murdoch |
| 3,403,679 | A | 10/1968 | Sinclair et al. |
| 4,093,108 | A | 6/1978 | Hein |
| 4,265,241 | A | 5/1981 | Portner et al. |
| 4,997,420 | A * | 3/1991 | LeFevre ............... A61M 5/145 128/DIG. 12 |
| 5,100,389 | A | 3/1992 | Vaillancourt |
| 5,271,527 | A | 12/1993 | Haber et al. |
| 5,346,476 | A | 9/1994 | Elson |
| 5,626,567 | A | 5/1997 | Gmeiner |
| 6,183,440 | B1 | 2/2001 | Bell |
| 6,277,099 | B1 | 8/2001 | Strowe et al. |
| 6,443,152 | B1 | 9/2002 | Lockhart et al. |
| 6,585,698 | B1 | 7/2003 | Packman et al. |
| 6,605,058 | B1 | 8/2003 | Wich |
| 6,641,561 | B1 | 11/2003 | Hill et al. |
| 6,648,859 | B2 | 11/2003 | Bitdinger et al. |
| 6,689,101 | B2 | 2/2004 | Hjertman et al. |
| 6,755,810 | B1 | 6/2004 | Buch-Rasmussen et al. |
| 6,979,316 | B1 | 12/2005 | Rubin et al. |
| 6,981,963 | B2 | 1/2006 | Barker et al. |
| 7,338,469 | B2 | 3/2008 | Barker et al. |
| 7,402,150 | B2 | 7/2008 | Matsumoto et al. |
| 7,708,719 | B2 | 5/2010 | Wilmot et al. |
| 7,717,877 | B2 | 5/2010 | Lavi et al. |
| 7,736,333 | B2 | 6/2010 | Gillespie, III |
| 7,927,303 | B2 | 4/2011 | Wyrick |
| 7,955,304 | B2 | 6/2011 | Guillermo |
| 7,976,514 | B2 | 7/2011 | Abry et al. |
| 8,038,649 | B2 | 10/2011 | Kronestedt |
| 8,062,255 | B2 | 11/2011 | Brunnberg et al. |
| 8,123,724 | B2 | 2/2012 | Gillespie, III |
| 8,162,917 | B2 | 4/2012 | Stepovich et al. |
| 8,235,952 | B2 | 8/2012 | Wikner et al. |
| 8,251,947 | B2 | 8/2012 | KraMer et al. |
| 8,308,695 | B2 | 11/2012 | Laiosa |
| 8,328,753 | B2 | 12/2012 | Solomon et al. |
| 8,361,025 | B2 | 1/2013 | Lawlis et al. |
| 8,523,807 | B2 | 9/2013 | Reynolds et al. |
| 8,597,257 | B2 | 12/2013 | Modi |
| 8,651,334 | B2 | 2/2014 | Suchan et al. |
| 8,672,901 | B2 | 3/2014 | Bollenbach et al. |
| 8,721,602 | B2 | 5/2014 | Poveda Estepa |
| 8,753,319 | B2 | 6/2014 | Davies et al. |
| 9,713,676 | B2 * | 7/2017 | Latham ............... A61M 5/20 |
| 2001/0056259 | A1 | 12/2001 | Skinkle et al. |
| 2003/0106824 | A1 | 6/2003 | Wilmot et al. |
| 2003/0216683 | A1 | 11/2003 | Shekalim |
| 2006/0275336 | A1 | 12/2006 | Du Plessis |
| 2008/0039789 | A1 | 2/2008 | Wyrick |
| 2008/0058732 | A1 | 2/2008 | Harris |
| 2008/0097308 | A1 | 3/2008 | Schiller et al. |
| 2009/0024083 | A1 | 1/2009 | Kriesel et al. |
| 2009/0112163 | A1 | 4/2009 | Bivin et al. |
| 2009/0182291 | A1 * | 7/2009 | Eilat ............... A61F 9/0026 604/290 |
| 2009/0198185 | A1 | 8/2009 | Gonnelli et al. |
| 2010/0036319 | A1 | 2/2010 | Drake et al. |
| 2010/0114059 | A1 | 5/2010 | Hiniduma-Lokuge et al. |
| 2010/0137832 | A1 | 6/2010 | Mathews et al. |
| 2010/0191217 | A1 | 7/2010 | Hommann et al. |
| 2010/0280460 | A1 | 11/2010 | Markussen |
| 2011/0213314 | A1 | 9/2011 | Guillermo |
| 2011/0218500 | A1 | 9/2011 | Grunhut et al. |
| 2011/0270220 | A1 | 11/2011 | Genosar |
| 2011/0282298 | A1 | 11/2011 | Agian et al. |
| 2012/0101475 | A1 | 4/2012 | Wilmot et al. |
| 2012/0123346 | A1 | 5/2012 | Davies et al. |
| 2012/0123387 | A1 | 5/2012 | Gonzalez et al. |
| 2012/0130318 | A1 * | 5/2012 | Young ............... A61M 5/2033 604/191 |
| 2012/0226238 | A1 | 9/2012 | Davies et al. |
| 2013/0041321 | A1 | 2/2013 | Cross et al. |
| 2013/0150800 | A1 * | 6/2013 | Kemp ............... A61M 5/2033 604/192 |
| 2013/0184677 | A1 | 7/2013 | Py |
| 2013/0197447 | A1 | 8/2013 | Smith |
| 2013/0197474 | A1 | 8/2013 | Bilton et al. |
| 2013/0211330 | A1 | 8/2013 | Pedersen et al. |
| 2013/0218089 | A1 | 8/2013 | Davies et al. |
| 2013/0218093 | A1 | 8/2013 | Markussen et al. |
| 2013/0225903 | A1 * | 8/2013 | Franci ............... B65B 3/003 600/4 |
| 2013/0226080 | A1 | 8/2013 | Davies et al. |
| 2013/0226081 | A1 | 8/2013 | Davies et al. |
| 2013/0226096 | A1 | 8/2013 | Jugl et al. |
| 2013/0296807 | A1 | 11/2013 | Lintern et al. |
| 2013/0296824 | A1 | 11/2013 | Mo et al. |
| 2014/0025014 | A1 | 1/2014 | Radmer et al. |
| 2014/0025015 | A1 | 1/2014 | Cross et al. |
| 2014/0031760 | A1 | 1/2014 | Mercer et al. |
| 2014/0066861 | A1 | 3/2014 | Auernhammer |
| 2014/0081239 | A1 | 3/2014 | Cronenberg |
| 2014/0088512 | A1 | 3/2014 | Quinn |
| 2014/0094757 | A1 | 4/2014 | Mercer et al. |

FOREIGN PATENT DOCUMENTS

| | | |
|---|---|---|
| EP | 0361668 B1 | 7/1994 |
| EP | 0609741 B1 | 5/1998 |
| EP | 0879611 B1 | 3/2001 |
| EP | 0906131 B1 | 1/2003 |
| EP | 0996476 B1 | 5/2003 |
| EP | 1024845 B1 | 7/2003 |
| EP | 1698364 B1 | 7/2008 |
| EP | 1927372 B1 | 6/2009 |
| EP | 2258426 A1 | 12/2010 |
| EP | 2436411 A1 | 4/2012 |
| EP | 2605814 A2 | 6/2013 |
| EP | 2704772 A1 | 3/2014 |
| FR | 1143900 A | 10/1957 |
| GB | 0906574 | 5/2009 |
| JP | H07-51367 A | 2/1995 |
| JP | 2011-524212 A | 9/2011 |
| WO | WO 2005075105 A1 | 10/1996 |
| WO | WO 2006057636 A1 | 10/1998 |
| WO | WO 2007034226 A1 | 4/1999 |
| WO | WO 0028941 A2 | 5/2000 |
| WO | WO 2011117592 A1 | 8/2005 |
| WO | WO 2012013585 A1 | 6/2006 |
| WO | WO 2012058192 A1 | 3/2007 |
| WO | 2009119496 A1 | 10/2009 |
| WO | 2010022870 A1 | 3/2010 |
| WO | WO 2013079652 A2 | 9/2011 |
| WO | WO 2013124139 A1 | 2/2012 |
| WO | WO 2014001319 A1 | 5/2012 |
| WO | WO 2014060563 A2 | 6/2013 |

(56) References Cited

FOREIGN PATENT DOCUMENTS

| WO | WO 2014076282 A1 | 8/2013 |
| WO | WO 2015121655 A1 | 1/2014 |
| WO | WO 9632344 A1 | 4/2014 |
| WO | WO 9842394 A1 | 5/2014 |
| WO | WO 2014080020 A1 | 5/2014 |
| WO | WO 9916485 A1 | 8/2015 |

OTHER PUBLICATIONS

PCT International Search Report and Written Opinion dated Apr. 5, 2013 for PCT/GB2011/000437 filed Mar. 25, 2011, 14 pgs.

Parisien, P. "A Practical Guide for the selection and use of prefilled Syringes for flushing vascular access devices", MEdXL Inc., Montreal, Canada.

PCT International Search Report and Written Opinion dated Mar. 4, 2014 for Intl. App. No. PCT/EP2013/074647, from which the instant application is based, 8 pgs.

\* cited by examiner

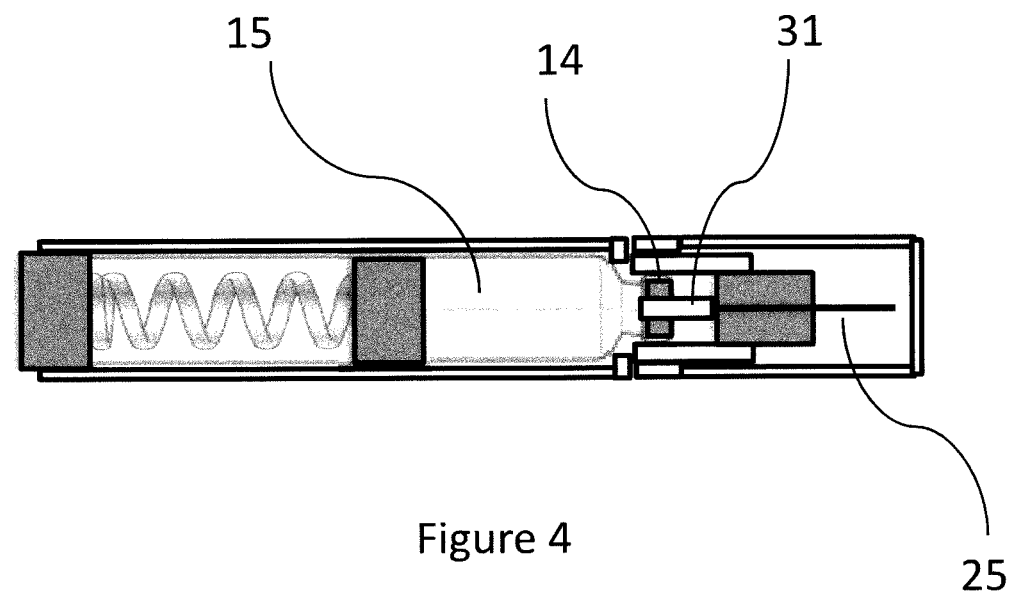
Figure 4
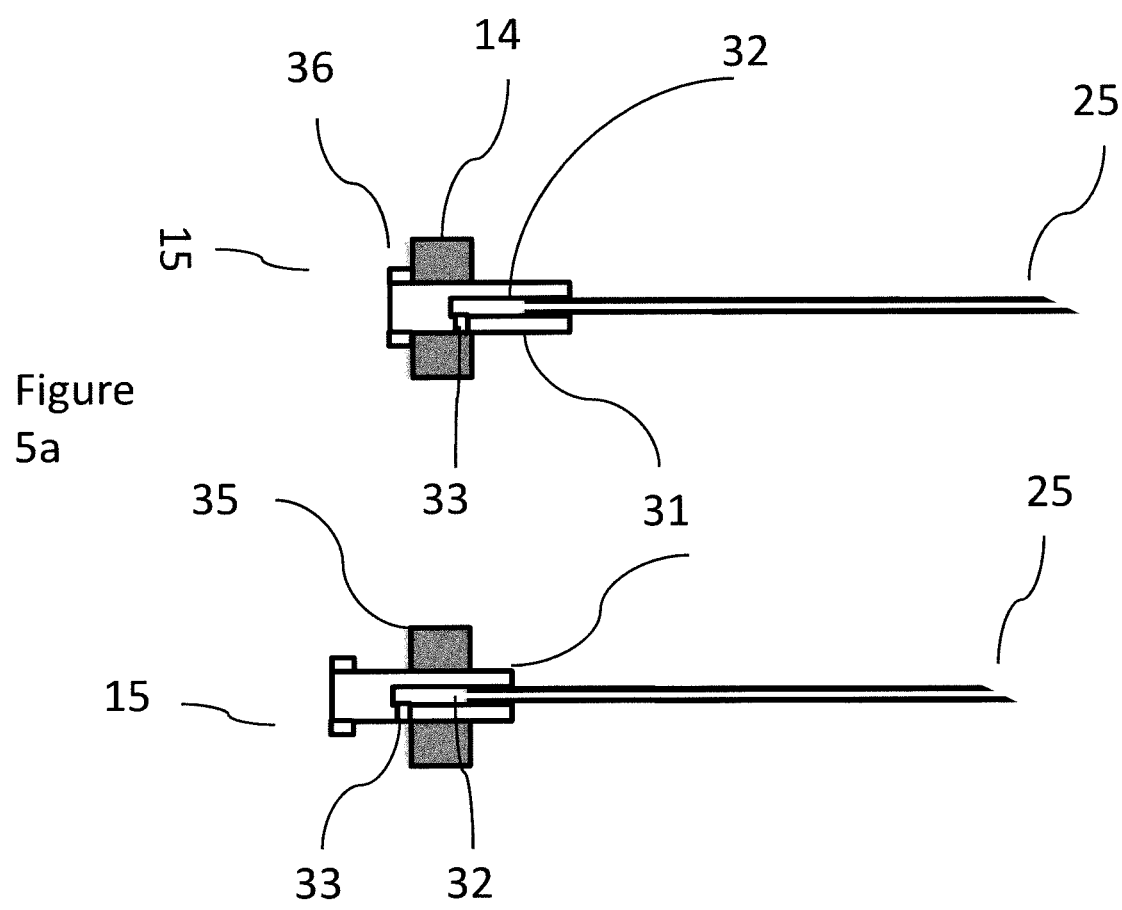
Figure 5a
Figure 5b

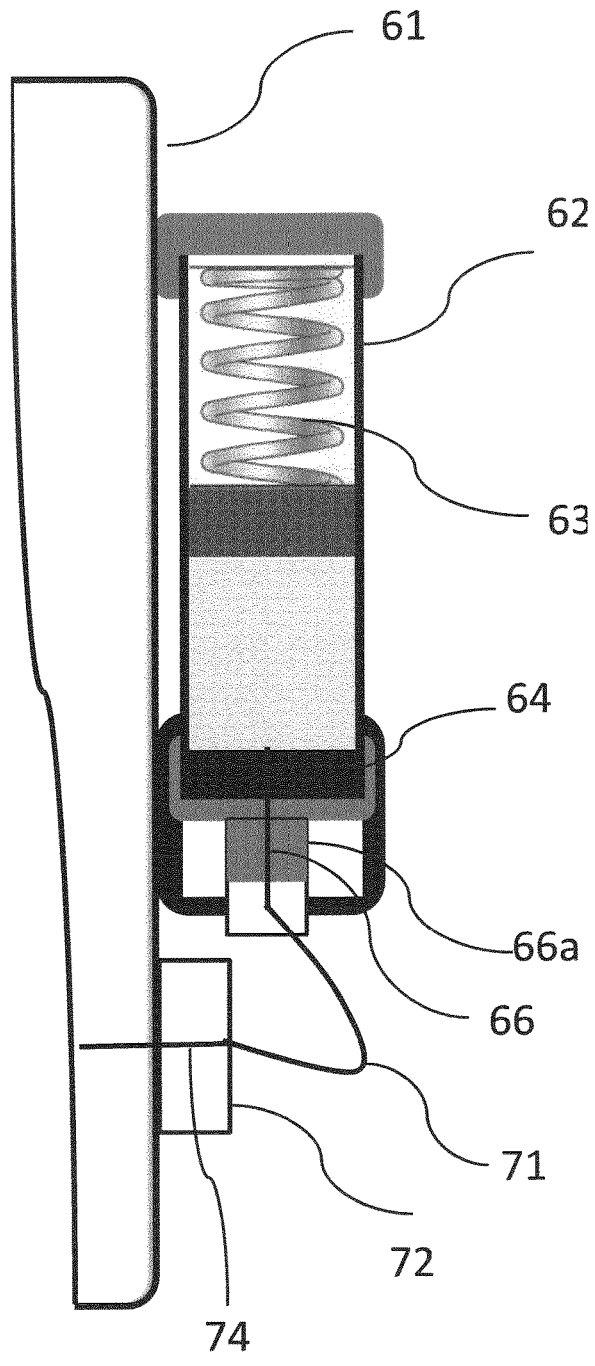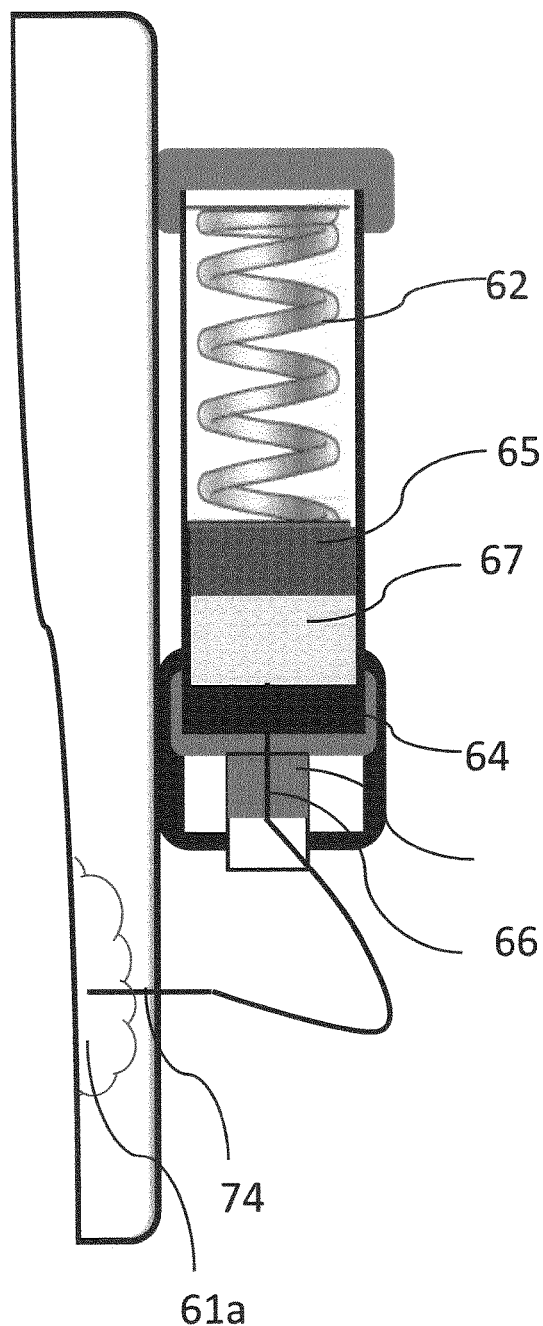
Figure 12c
Figure 12d

AUTO-INJECTOR ASSEMBLY

RELATED APPLICATIONS

This application is a 35 U.S.C. 371 national stage filing from International Application No. PCT/EP2013/074647, filed Nov. 25, 2013 and claims priority to British Application Nos. 1221086.0, filed Nov. 23, 2012; 1222426.7, filed Dec. 13, 2012; 1304392.2, filed Mar. 12, 2013; 1306062.9, filed Apr. 4, 2013; and 1306382.1, filed Apr. 9, 2013; the teachings of each of which are incorporated herein by reference.

The invention relates to an auto-injector assembly that may be used by the patient for self-injection or by a medical professional.

BACKGROUND

Pre-filled containers, such as pre-filled syringes and pre-filled cartridges, are filled by manufacturers in controlled sterile environments, eliminating the need for a patient or a medical professional to fill them from vials or ampoules prior to use. Pre-filled syringes typically have life storage of two years or more.

Auto-injectors comprising pre-filled syringes provide automation of the injection stroke, alleviating the need for the patient or medical professional to actuate a plunger rod to deliver medication.

Industry standard 'staked needle' pre-filled syringes, such as the BD Hypak, the Gerresheimer RTF or ClearJect, the Schott TopPak, the Daikyo Crystal Zenith® Syringe, and other commercially available glass or plastic ready to fill syringes, are commonly used as the primary pack or primary container for auto-injectors.

Historically the industry has been reliant upon these well-established off-the-shelf primary containers, usually the glass versions. Most of the alternative auto-injector technologies require a bespoke primary container, which introduces unwanted risk and cost to the development process. However, the standard glass pre-filled syringe and to a lesser extent the glass cartridge, present a number of problems.

- They are fragile and not well suited to use in spring-driven auto-injector devices. A pressure spike or pulse created when the auto-injector spring hits the syringe stopper or piston can cause chipping or breakage of the syringe.
- Glass is dimensionally difficult to control during syringe manufacture, so syringe tolerances are broad. This is especially true of the length, making it difficult to design an auto-injector device to fit round it.
- The epoxy glue used in staked needle syringes typically used in auto-injectors can interact with the drug.
- Syringe nozzles are typically formed over a tungsten pin. Residue of the tungsten pin can interact with the drug during storage.
- The drug contained within a pre-filled syringe is in contact with the needle metal during prolonged storage, which can cause drug stability problems.
- The drug is typically in contact with a needle metal during prolonged storage, and this requires a rubber cap, or 'boot', to close the opening at the needle tip. Application or removal of the rubber cap can lead to needle damage.
- The container stopper or piston has four functions: drug delivery, oxygen barrier, humidity barrier and sterility barrier. This results in a need for complex multi-ribbed components that form a tight seal with the container chamber. This tight seal results in a need to lubricate the inside of the chamber, for example by siliconisation to minimize friction and to prevent the piston or stopper sticking to the chamber during long storage times.
- Siliconisation (i.e. treatment with a silicone coating or oil) may cause stability problems with the drug contained in the pre-filled syringe or cartridge.

Plastic cartridges and pre-filled syringes used as primary containers also have a number of disadvantages, which include:

- They need to be manufactured in clear plastic with high oxygen barrier properties, which are always inferior to glass.
- Because of the high oxygen barrier requirement, plastic pre-filled cartridges or syringes are expensive relative to glass pre-filled cartridges or syringes.
- Extractables and leachables from the plastic forming the cartridge or syringe are higher than in glass containers. Extensive testing is required before they can be safely used.
- The candidate plastics are not as 'known' as glass. This results in an industry reluctance to adopt them.
- As with glass pre-filled containers, the drug contained within the pre-filled container is in contact with the needle metal during prolonged storage, which can cause drug stability problems.
- The drug is typically in contact with a needle metal during prolonged storage, and this requires a rubber cap, or 'boot', to close the opening at the needle tip. Application or removal of the rubber cap can lead to needle damage.

Both glass and plastics syringes can only be filled without gas bubbles if they are vacuum stoppered, which slows the filling line down considerably.

Various patents describe devices that try to overcome some of the above problems, notably the wet needle. Most of the prior art involves a completely new primary pack which the industry is reluctant to use. For instance US20120130318 A1 describes a device with a diaphragm to keep the needle dry, but which requires a completely new primary pack.

Another trend in the industry is that so called small molecule drugs, or conventional drugs, are being replaced by large molecule biopharmaceutical (biological) drugs. This trend has accelerated the need for alternative delivery systems with dry needles, reduced silicone lubrication, no tungsten residue, and good oxygen barrier properties, and in some cases larger volumes than traditionally injected.

The vast majority of biological drugs have to be administered parentally. Most protein drug formulations are destroyed by digestive enzymes if taken orally, and it is difficult to get sufficient active dosage to transfer across a mucous membrane or epithelium, so the bioavailability is typically low. All antibody drugs will be for parenteral administration for the foreseeable future. Most injections and infusions have never been particularly popular with the recipient. They hurt, or at least they are perceived to hurt especially if the needles are of large diameter.

Many biological drugs are more viscous than small molecule drugs. That makes them more difficult to inject, as either larger diameter needles are required to minimize flow resistance, or much higher pressures are required if the favoured small needles are used. This can lead to breakage of containers.

One solution is to dilute the highly viscous drug reducing its viscosity. If this is done the total volume can exceed the maximum acceptable injectable amount of about 1.5 ml. To inject larger volumes in excess of 1.5 ml, patch or bolus pumps are used.

DESCRIPTION OF INVENTION

The invention provides an auto-injector assembly and method of producing an auto-injector assembly as defined in the appended independent claims, to which reference should now be made. Preferred or advantageous features of the invention are set out in dependent sub-claims.

Thus, an auto-injector assembly may comprise a medicament container defining a substantially cylindrical chamber containing a liquid medicament, a proximal end of the chamber being closed by a piston slidably located within the cylindrical chamber, and a distal end of the chamber being closed by a container seal spanning an opening at a distal end of the medicament container. The medicament container may be, for example, a cartridge or a syringe. A biasing means or mechanism is coupled to the piston and acts to bias the piston towards the container seal, thereby pressurising the liquid medicament. The assembly further comprises a hypodermic needle for parenteral administration of the liquid medicament, and a removable needle cap for maintaining the hypodermic needle in sterile conditions until use. Means for establishing fluid communication between the chamber and the hypodermic needle is also provided, such that the pressurised liquid medicament is automatically delivered through the hypodermic needle when communication has been established.

Preferably the removable needle cap does not contact the hypodermic needle. This avoids the problems of bending and blunting the needle that result from the use of a rubber boot to seal the distal end of the hypodermic needle in current auto-injectors.

The present invention allows for the use of industry standard injection cartridges or ready to fill syringes (pre-filled syringes) as medicament containers to create auto-injectors and bolus pumps (large volume injectors) that have dry needles during storage and various other advantages. The present invention allows for the injection of larger volumes of drugs than can be achieved using most auto-injectors.

Both plastic and glass versions of standard injection cartridges and ready to fill syringes are available from a number of suppliers including Gerresheimer, Schott and Becton Dickinson.

In the present invention the cartridges or ready to fill syringes may be filled using conventional filling lines used to fill standard injection cartridges and ready to fill syringes. Preferably, the container seal is a pierceable septum spanning the opening at the distal end of the container. The container seal may be a polymeric or elastomeric septum coupled to the opening at a distal end of the medicament container by a metal crimp.

In preferred embodiments, a conventional rubber septum may be crimped to the container neck after filling. Thus, there is no change at all to the standard filling procedure currently used, and no change at all to the container primary pack, for example a cartridge or syringe primary pack.

Syringes are filled from behind and then the piston or stopper is inserted to retain the contents. Again, the present invention does not call for a change to the filling procedure if the medicament container is a standard syringe. The only difference in the primary pack is that a septum replaces the staked needle or cap that is traditionally used at the nozzle end of the syringe. In the case of ready to fill syringes, a Luer-type Lock can be used, with a seal or septum held by a Luer Lock fitting.

Glass injection cartridge dimensions and tolerances are defined in International Standard ISO 13926-1. Stoppers and seals (cap and disc) are described in International Standard ISO 13926-2 and 3. Ready to fill syringes or pre-filled syringes dimensions and tolerances are defined in ISO 11040-4.

Preferably the means for establishing fluid communication is a valve comprising a valve housing defining a bore. The valve housing may be coupled to the distal end of the container such that the pierceable septum is located at a proximal end of the bore. A shuttle may be slidably retained within the bore, the shuttle comprising a piercing element for piercing the pierceable septum when the shuttle is moved towards the proximal end of the bore in order to establish fluid communication between the chamber and the hypodermic needle.

The pierceable septum is disposed between the liquid medicament and the needle, and the needle, therefore, does not contact the liquid medicament until the moment of delivery. Undesirable drug interactions are thereby avoided. The valve is preferably able to be coupled to a standard filled container.

The piercing element is preferably a hollow needle extending from a proximal surface of the shuttle and disposed in fluid communication with the hypodermic needle. Thus, when the hollow needle pierces the septum, the pressurised liquid medicament is able to flow into the hollow needle and onwards to the hypodermic needle.

In preferred embodiments the hypodermic needle extends from a distal surface of the shuttle. Thus, the hypodermic needle may move with the shuttle. It may be particularly convenient if the piercing element and the hypodermic needle are formed by opposite ends of a double-ended needle located by the shuttle. Where both the piercing element and the hypodermic needle are located by the shuttle, the pierceable septum may be pierced when a force is applied to the shuttle by the patient's skin at the injection site. This may occur, for example, when the hypodermic needle has been inserted to the appropriate depth in the patient and a portion of the shuttle comes into contact with the patient's skin.

Preferably, the valve housing is sealingly coupled to the container such that the piercing element is maintained in sterile conditions until use. For example, a sealing element such as an o-ring may be employed to ensure that the piercing element is maintained in sterile conditions after production of the auto-injector assembly. Where the seal is a crimped septum, the valve housing may be sealingly coupled to an external radial surface of the metal crimp.

In another embodiment, the container seal may comprise an elastomeric septum spanning the opening at the distal end of the container, the elastomeric septum defining a through-hole sealed by a proximal end of a slidable valve stem retained by the elastomeric septum. The valve stem defines a valve stem channel in communication with the hypodermic needle. The means for establishing fluid communication is a valve comprising a valve housing defining a bore, the valve housing coupled to the distal end of the container such that the elastomeric septum is located at a proximal end of the bore. A shuttle slidably retained within the bore locates the valve stem such that, when the shuttle is moved towards the proximal end of the bore, a cross-hole defined in the valve stem allows liquid to pass into the valve stem channel to establish fluid communication between the chamber and the hypodermic needle. Such an embodiment may avoid the need for a septum to be pierced to deliver the medicament.

It is preferable that the medicament container is pressurized after filling by a spring, which biases the piston or stopper such that the liquid medicament stays pressurized during its shelf life. Thus, it is preferable that the piston is coupled to a spring for biasing the piston towards the container seal.

In preferred embodiments, the auto-injector assembly comprises a cap for sealing a proximal end of the medicament container, and a spring is retained between the cap and the piston to exert a force urging the piston towards the container seal. Such a cap may seal the chamber of the medicament container against oxygen and/or humidity.

In other preferred embodiments the auto-injector assembly further comprises a casing that surrounds a substantial portion of the medicament container. The casing engages with a proximal portion of the medicament container, for example at a neck or a shoulder of the container, and the spring is retained between a portion of the casing and the piston to exert a force urging the piston towards the container seal. Preferably, the casing seals the chamber of the medicament container against oxygen and/or humidity. Preferably, the casing comprises windows for viewing the medicament container.

In some embodiments, the means for establishing fluid communication between the chamber of the medicament container and the hypodermic needle may comprise a length of flexible tubing. Such embodiments may be preferred when a large volume of drug is to be administered.

Conventional auto-injector assemblies do not contain a liquid medicament that is stored under pressure. Thus, the piston or stopper that seals the container may move as the liquid and/or air within the container expands and contracts. By applying a pressure to the piston that constantly urges the piston towards the container seal, the amount of piston movement may be reduced. This may be a particular advantage during air transport. Reducing the piston movement during air transport may reduce the risk of contamination or loss of sterility. Additionally, because the liquid medicament contents are under positive pressure relative to atmosphere at all times, there is less likelihood of foreign matter entering the sterile environment and contaminating the drug. This is particularly important as drugs formulations for injectables cannot generally include any preservatives.

The fact that the piston is constantly biased towards the container seal also provides delivery advantages. The liquid medicament is delivered through the hypodermic needle as soon as fluid communication is established between the container chamber and the hypodermic needle. In conventional auto-injectors an actuation force, for example provided by a spring, is brought into contact with the piston or stopper to deliver the medicament. This causes a pressure spike or peak which may cause user discomfort and may damage the container. Container damage is a particular risk in an auto-injector using industry standard glass primary packaging. Because the liquid is maintained under constant pressure in the present invention, an auto-injector assembly may be simplified. For example, there is no need to introduce damper mechanisms to ameliorate the activation pressure pulse. There is also no need to deliberately fill the container with an air bubble to minimize the activation pressure pulse.

A constant pressurisation of the liquid medicament advantageously provides for automatic leak detection. It is important to know whether a medicament has leaked, as any leak may be a site of contamination. Further, a leaked medicament may not provide a patient with a full required dose. Where the liquid is under constant pressure during storage, due to the piston being biased towards the container seal, any leak will result in the liquid medicament being expelled from the assembly and detected by causing the piston to visibly move to a non full dose position thus alerting the user.

Thus, the advantages of storing the drug under pressure include:

1—Leak detection. If the primary container or closure is damaged the drug will leak and the stopper movement alerting the user to a problem.

2. —Stopper movement due to any gas bubble and pressure decrease during air transport is much reduced as the pressure ratio is much reduced.

3—Containers can be filled without gas bubbles by overfilling and washing.

4—The positive pressure in the container during storage minimizes the risk of drug contamination and loss of sterility.

Other advantages of the an auto-injector assembly as described herein include:

A—Dry Needle. The container seal ensures the needle is dry and not in contact with drug during storage. This eliminates blockage problems due to crystallization and drug interaction with the needle steel. The glue used to fix the needle in place in standard pre-filled syringes is not present, thereby avoiding glue/drug interactions.

B—Containers can be made without the use of tungsten pins, which is not the case, for example, with pre-filled syringes that use staked needles. Tungsten residues can interact with biological drugs. The distal opening of a container is spanned by a container seal and is wide enough that it does not require a tungsten pin for its formation.

C—No spring impact—no pressure peak. Pressure decreases rather than increasing at start of injection leading to a gentle injection. In standard auto-injectors the drug is only pressurised at the time of the injection when the actuation spring is released. This often leads to broken syringes.

D—Glass barrel length tolerance insensitive—This is due to the spring being held relative to the container, for example the cartridge or syringe, rather than the device casing as in conventional auto-injectors.

E—No pressure absorbing gas bubble is required to act as 'shock absorber' as in conventional pre-filled syringe based auto-injectors.

F—No needle boot, which contacts the needle, is required, as the needle is dry during storage. Thus, there is no needle damage such as bending and blunting during assembly. This means smaller needles can be used with the present invention such as 30G. Lower needle cap pull off forces are required, as only a sterile cap is needed. The sterile cap is not in contact with the needle.

G—The device can be filled and capped on standard lines without any modifications.

Filled cartridges or pre-filled syringes may be converted into auto-injectors (including bolus pumps, patch pump, and large volume injectors) with manual needle insertion and retraction, or auto needle insertion and retraction, or any combination thereof.

The auto-injector will preferably have a safety needle shield to protect patients and others. Preferably this will be a passive (automatic) shield.

The invention may be used in conjunction with a safety needle, such as the West Novaguard, TIP TOP or any other such device.

Fill volumes of at least between 0.1 ml to 20 ml are possible.

Both glass and plastic cartridges or ready to fill syringes may be used or any other primary pack of any material that is suitable may also be used.

The invention may be used in a reusable device (a reusable auto-injector).

A method of producing an auto-injector assembly may comprise the steps of, filling a medicament container with a liquid medicament and sealing the liquid medicament within the container by applying a container seal to a distal opening of the container. The liquid medicament is retained within the medicament container under pressure, for example as provided by a biasing means such as a spring. A hypodermic needle is coupled to the container via a means for establishing fluid communication between the liquid medicament and the hypodermic needle. The hypodermic needle is protected with a removable needle cap for maintaining the hypodermic needle in sterile conditions until use. The needle cap doe not contact the needle. A valve housing is coupled to the container such that a piercing element for piercing the container seal is maintained in sterile conditions until use. The production steps are carried out in a sterile environment. The auto-injector assembly may be any described above.

The following describes the use of an auto-injector assembly as described above having a pierceable septum and a piercing means and hypodermic needle both located by a movable shuttle. The removable needle cap is removed, thereby exposing the hypodermic needle. The needle is then inserted into the patient. The insertion force of the needle into the patient is preferably lower than the force required to pierce the septum. Once the needle has been inserted to an appropriate depth, a face of the shuttle contacts the patients skin. Continued pressure causes the piercing element to penetrate the septum and initiate fluid communication between the container chamber and the hypodermic needle. Alternatively a needle safety shield is in contact with the patients skin during injection and this in turn engages with the piercing element causing it to penetrate the septum. A biasing force, preferably applied by a helical spring, forces the liquid medicament out of the container and into the patient.

The present invention may be used in conjunction with any drug whether a solution or a suspension or a mixture of these of any viscosity and density.

Any of the drugs listed below may be injected using the invention either on its own or a mixture thereof:

17-alpha hydroxyprogesterone caproate, Corticotropin (ACTH), Laronidase, Factor VIII, Von Willebrand Factor Complex, Alefacept, Apomorphine Hydrochloride, Darbepoetin Alfa, Nelarabine, Bevacizumab, Interferon beta-1a, 11 mcg, Interferon beta-1a, 33 mcg, Factor IX complex, Interferon beta-1b, Ibandronate Sodium, Botulinum Toxin, Protein C Concentrate, Alglucerase, Imiglucerase, Injection, Secretin, Synthetic, Human, 1 Microgram, Glatiramer acetate, Decitabine, Desmopressin acetate, Idursulfase, Etanercept, Epoetin alfa, Anadalufungin, Cetuximab, Ethanolamine Oleate, Hyaluronic acid derivatives, Agalsidase beta, Factor IX non-recombinant, Factor IX recombinant, Factor VIII (human), Factor VIII (porcine), Factor VIII recombinant, Feiba VH, Immune globulin (intravenous) (IVIG), Enfuvirtide, Immune globulin (intravenous) (IVIG), Somatropin, Hepatitis B Immune, Globulin (intravenous) (IVIG), Trastuzumab, von Willebrand factor complex, Adalimumab, Insulin for administration through DME (i.e., insulin pump), Hyaluronic acid derivatives, Mecasermin, Gefitinib, Levoleucovorin calcium, Ranibizumab Injection, Pegaptnib, Urofollitropin, Micafungin, Botulinum toxin type B, Aglucosidase alfa, Galsulfase, Somatropin, Factor Vila, Atacept, Hyaluronic acid derivatives, Hyaluronan derivative, Immune globulin (intravenous) (IVIG), Hemin, Peginterferon alfa-2a, Peginterferon alfa-2b, Epoetin alfa, Somatrem, Efalizumab, Interferon beta-1a, subq, Zoledronic Acid, Infliximab, Treprostinil, Fluocinolone acetonide, intravitreal implant, Zidovudine, Eculizumab, Lanreotide, Histrelin implant, Palivizumab, Hyaluronic acid derivatives, Temozolomide, Antithrombin III (Human), Natalizumab, Panitumumab, Immune globulin (intravenous) (IVIG), Azacitidine, Verteporfin, Hyaluronidase, Bovine, Preservative Free, Naltrexone Depot, Teniposide, Omalizumab, 90Y-Ibritumomab tiuxetan, ADEPT, Aldesleukin, Alemtuzumab, Bevacizumab, Bortezomib, Cetuximab, Dasatinib, Erlotinib, Gefitinib, Gemtuzumab, Imatinib, Interferon alpha, Interleukin-2, Iodine 131 tositumomab, Lapatinib, Lenalidomide, Panitumumab, Rituximab, Sorafenib, Sunitinib, Thalidomide, Trastuzumab;

Plus other biologics or small molecule drugs including a wide range of medicinal products such as vaccines, blood and blood components, allergenics, somatic cells, gene therapy, tissues, and recombinant therapeutic proteins, and substances that are (nearly) identical to the body's own key signalling proteins may also be injected using the invention. Examples are the blood-production stimulating protein erythropoetin, or the growth-stimulating hormone named (simply) "growth hormone" or biosynthetic human insulin and its analogues.

Plus monoclonal antibodies. These are similar to the antibodies that the human immune system uses to fight off bacteria and viruses, but they are "custom-designed" (using hybridoma technology or other methods) and can therefore be made specifically to counteract or block any given substance in the body, or to target any specific cell type.

Plus Receptor constructs (fusion proteins), usually based on a naturally-occurring receptor linked to the immunoglobulin frame. In this case, the receptor provides the construct with detailed specificity, whereas the immunoglobulin-structure imparts stability and other useful features in terms of pharmacology.

Plus any of the following:
Alpha1-Adrenergic Antagonists, Analgesic Agents, Anesthetics, Angiotensin Antagonists, Inflammtory Agents, Antiarrhythmics, Anticholinergics, Anticoagulants, Anticonvulsants, Antidiarrheal Agents, Antineoplastics and Antimetabolites, Antineoplastics and Antimetabolites, Antiplasticity Agents, Beta-Adrenergic Antagonists, Bisphosphonates, Bronchodilators, Cardiac Inotropes, Cardiovascular Agents Central Acting Alpha2-stimulants, Contrast Agents, Converting Enzyme Inhibitors, Dermatologics, Diuretics, Drugs for Erectile Dysfunction, Drugs of Abuse, Endothelin Antegonists, Hormonal Agents and Cytokines, Hypoglycemic Agents Hypouricemic Agents and Drugs Used For Gout, Immunosuppressants, Lipid Lowering Agents, Psychotherapeutic Agents, Renin Inhibitors, Serotonergic Antagonist Steroids, Sympathomimetics, Thyroid and Antithyroid Agents, Vasodilators, Vasopeptidase Inhibitor Or any other drug not listed above capable of being injected and available at present or being developed by any pharmaceutical company or any other company anywhere in the world.

Plus any drug with indications for Rheumatoid arthritis or Multiple sclerosis.

Or any drug approved and listed by the FDA in the USA or any other national or international agency. Additionally any generic or biosimilar drug on the market or in development.

Or any one of the following: Lipitor, a cholesterol-lowering statin drug, Nexium, an antacid drug, Plavix, a blood thinner, Advair, Abilify, an antipsychotic drug, Seroquel, an antipsychotic drug, Singulair, an asthma drug; Crestor, a cholesterol-lowering statin drug, Actos, a diabetes drug or Epogen, an injectable anemia drug.

The invention may be used to inject humans or animals.

Specific embodiments of the invention will now be described with reference to the figures, in which:

FIG. 4 is a schematic illustration of an auto-injector assembly according to an embodiment of the invention;

FIGS. 5a and 5b illustrate details from the auto-injector of FIG. 4;

FIGS. 12a to 12d illustrate the use of an auto-injector assembly according to an embodiment of the invention.

to FIG. 12 describe some embodiments of the invention. Others are possible and within the spirit of the invention.

Figure 1:
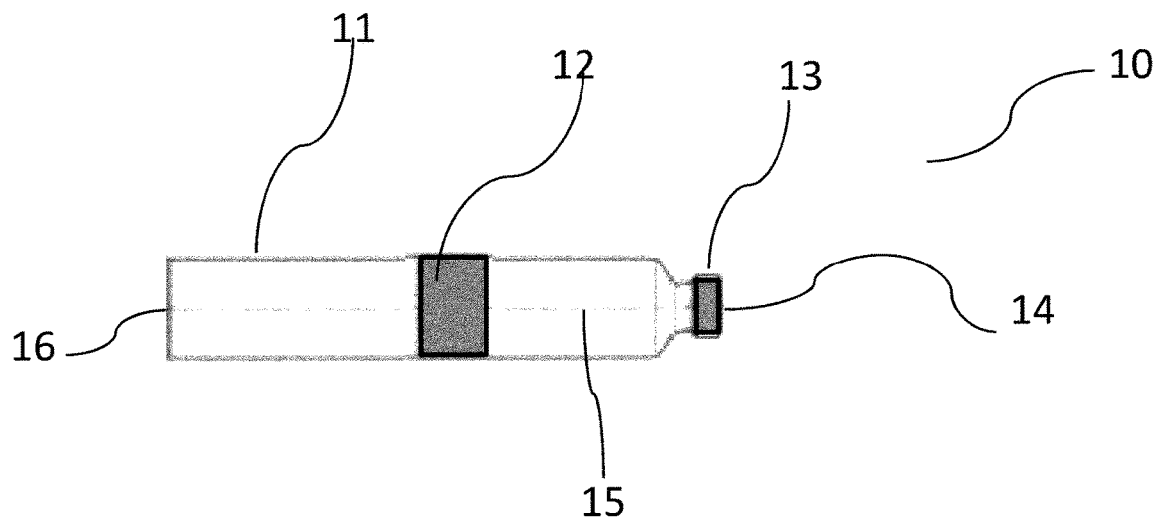
FIG. 1 is a schematic illustration of a standard pre-filled cartridge as typically used in the pharmaceutical industry, and suitable for use as a medicament container in an auto-injector assembly according to an embodiment of the invention.

FIG. 1 illustrates a standard cartridge 10 used in the pharmaceutical industry, for example for dental injections and insulin injections. A cartridge body or barrel 11 has a liquid drug solution or suspension 15 within. The liquid 15 is contained within a cartridge chamber defined by a movable piston or stopper 12 at one end (towards a proximal end of the cartridge) and a container seal in the form of a rubber seal or septum 14 held into place by a metal crimp 13 at the other end (a distal end of the cartridge). The barrel 11 is open at its proximal end 16. The cartridge 10 may act as the primary pack in an auto-injector assembly according to an embodiment of the invention.

Figure 2:
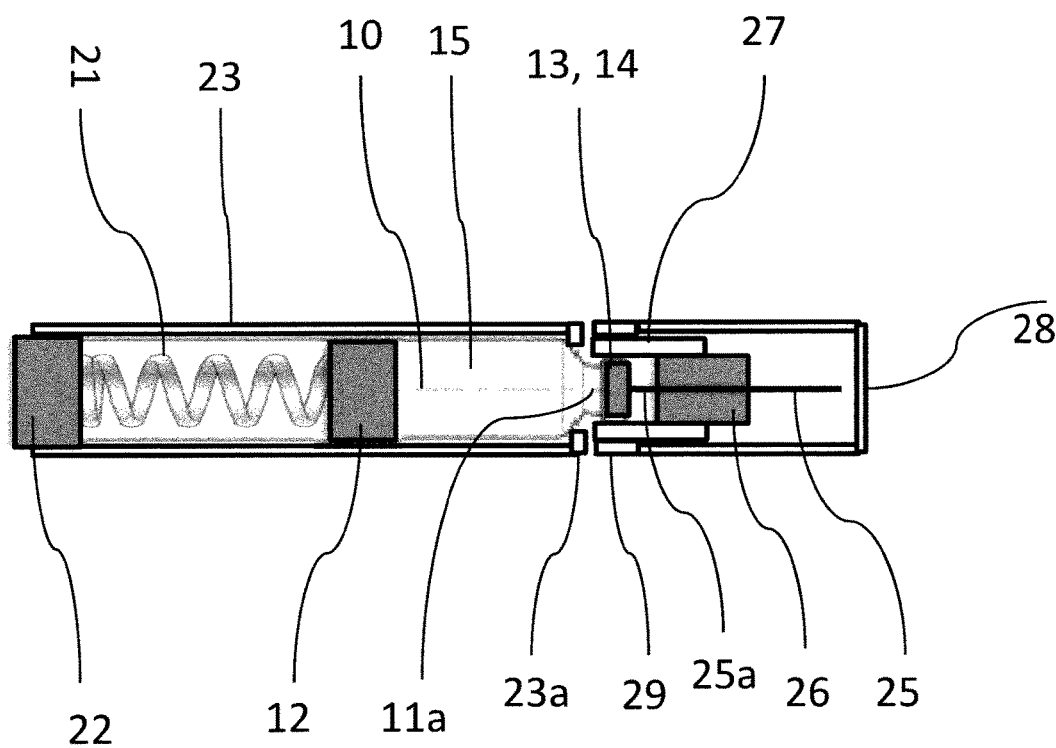
FIG. 2 is a schematic illustration of an auto-injector assembly according to an embodiment of the invention.

FIG. 2 shows the use of the cartridge 10 of FIG. 1 as a primary container in an auto-injector assembly. The assembly has a helical spring 21 acting to pressurise the liquid contents 15 of the cartridge 10 by urging the stopper 12 forward in a direction towards the rubber septum 14. The spring 21 is located by a spring lock or cap 22, which in turn is held into place by a casing 23. The casing 23 has lugs 23a which are engaged with the cartridge neck 11a.

The casing 23 has viewing holes (not shown) in order to inspect the drug before injection.

A valve housing 27 is sealed against a radially external portion of the metal crimp 13. The valve housing locates a slidable shuttle 26, itself locating two needles that are in fluid communication with each other. A hypodermic needle 25 extends from a distal end of the shuttle 26 for injecting the patient, and a hollow needle 25a extends from a proximal end of the shuttle 26 for perforating the septum 14. In use, the shuttle 26 is held against the patient's skin after inserting the hypodermic needle 25 into the patient. The shuttle slides within the valve housing and the hollow needle 25a is forced through the septum 14. This action results in establishment of fluid communication between the cartridge chamber and the hypodermic needle 25. Because the liquid contents 15 of the chamber are pressurised, the liquid flows into the patient via the needles 25a and 25.

The needles 25a and 25 may be formed as a single double-ended needle or as separate needles connected by a channel defined through the shuttle 26.

A sterile removable needle cap 28 keeps the hypodermic needle 25 sterile before use for injection.

The spring lock 22 may form an oxygen and humidity barrier, in which case the stopper 12 need not be itself an oxygen and humidity barrier. This may allow for a greater choice of materials for the stopper, including self lubricating materials such as PTFE and Silicone. Self lubricating materials may eliminate or reduce the requirement to lubricate the internal surfaces of the cartridge to enable the stopper to slide.

Since the spring lock 22 is not in contact with the drug, a wide range of barrier materials can be used in its manufacture. Barrier materials may be available that were not previously available for use as a stopper, due to contact between the stopper and the drug.

The spring lock 22 may be held in place by an outer casing or any other means such as a flange formed as part of the syringe or cartridge barrel.

In the embodiment of FIG. 2, the liquid drug is stored in an unmodified standard cartridge. This provides the advantage that no new stability trials are needed with existing drugs.

Figure 3:
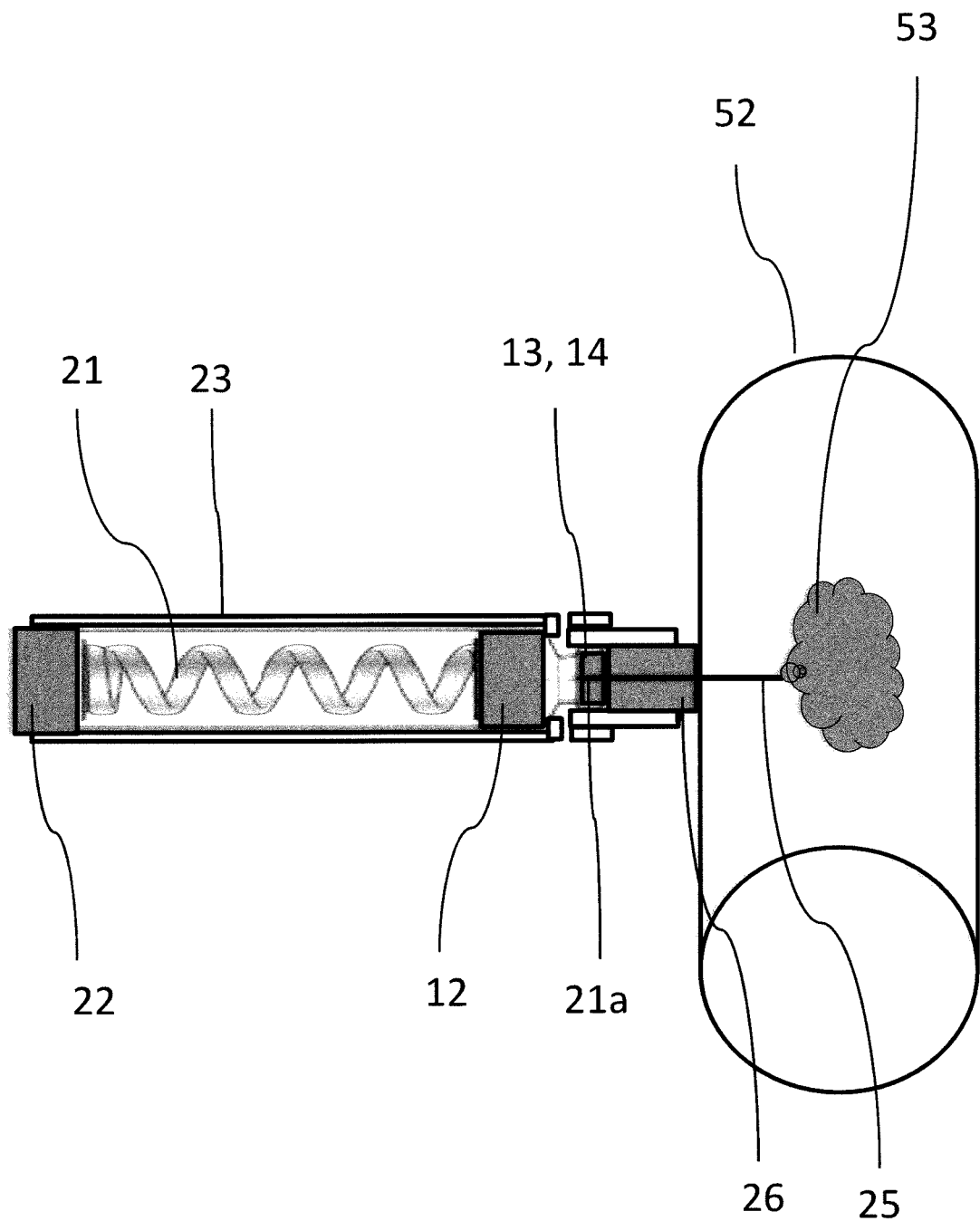
FIG. 3 illustrates the use of the auto-injector assembly of FIG. 2.

FIG. 3 illustrates use of the auto-injector assembly of FIG. 2. The hypodermic needle 25 has penetrated an injection site 52. The hollow needle 25a has pieced the septum 13 and the stopper 12 has pushed the liquid drug contents out of the cartridge under the action of the spring 21. The liquid medicament contents have been delivered 53. The spring 21 is now extended and the stopper has been moved to a distal end of the cartridge.

In FIG. 4 an auto-injector assembly having an alternative valve system is shown. A valve stem 31 is sealingly mounted in a septum 14 and connected to a hypodermic needle 25.

FIG. 5 show the needle/valve arrangement of the embodiment of FIG. 4 in greater detail. In FIG. 5a it can be seen that the valve stem 31 defines a channel 32 that is in communication with the hypodermic needle 25. The valve stem also defines a cross hole 33 which is closed by the septum 14 when valve is closed. The valve stem 31 has a shoulder 36 to prevent it from being pushed out of the septum before use by the pressurised contents 15 of the cartridge.

FIG. 5b illustrates the valve in an open position. The cross hole 33 is now free of the septum 14. This results in establishment of fluid communication between the cartridge chamber and the hypodermic needle 25. Because the liquid contents 15 of the chamber are pressurised, the liquid flows into the patient via the channel 32 and the hypodermic needle 25.

Figure 6:
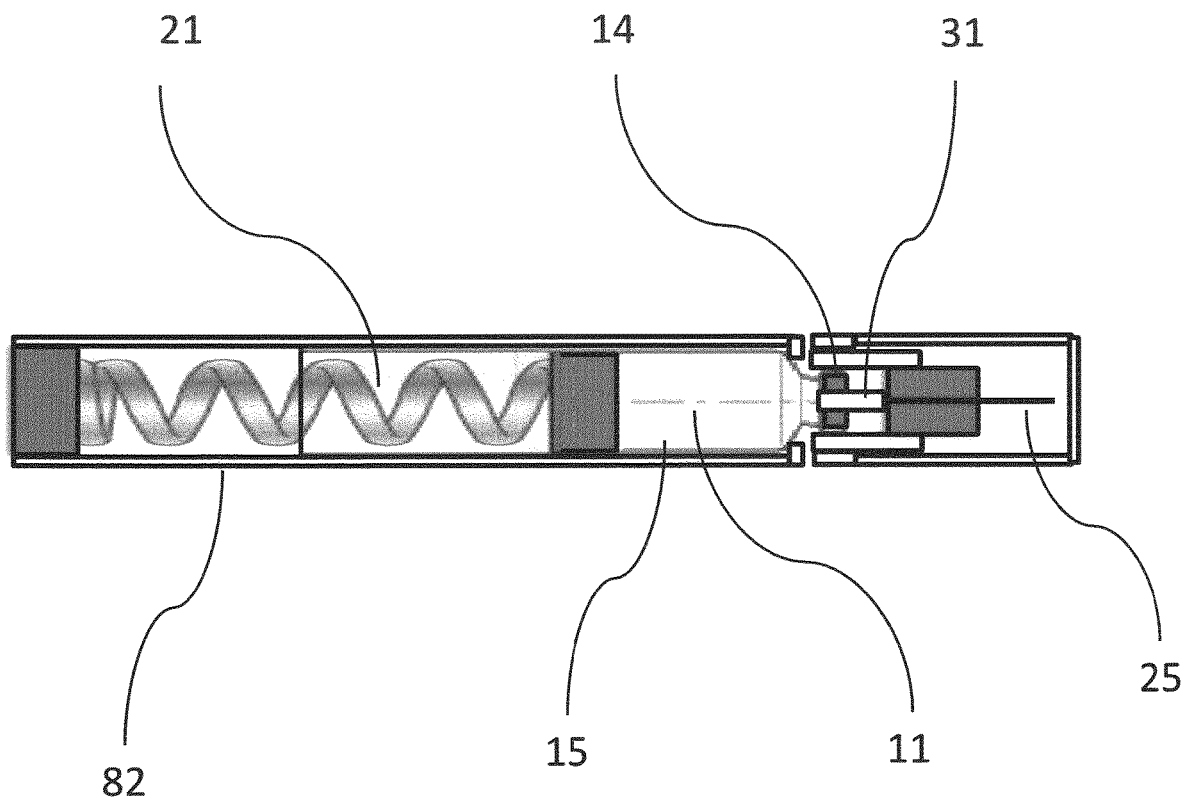
FIG. 6 is a schematic illustration of an auto-injector assembly according to an embodiment of the invention.

FIG. 6 illustrates an auto-injector assembly in which a spring 21 held within the cartridge barrel 11 by a spring holder 82, which is formed to hold part of the spring 21 within. In this way the contents 15 within the barrel 11 can be of larger volume than if the spring was entirely located within the barrel 11, as in shown in FIGS. 2 to 5.

In other embodiments the spring may be held in place by a casing.

Figure 7:
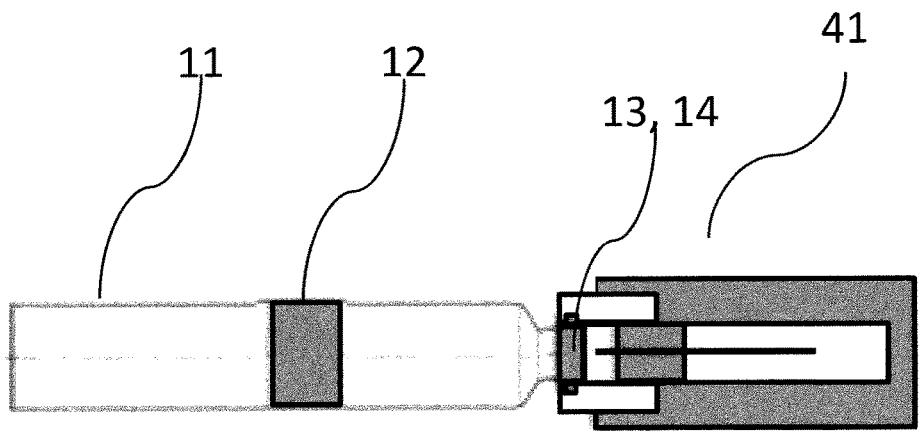
FIG. 7 is a schematic illustration of an auto-injector assembly according to an embodiment of the invention.

FIG. 7 illustrates a cartridge 11 with a stopper 12 and an attached sterile needle assembly 41. The needle assembly 41 is sealingly attached to the cartridge 11 in a sterile and clean environment, preferably soon after the cartridge 11 is filled and the septum 14 is crimped on with a metal crimp or ferrule 13.

Figure 8:
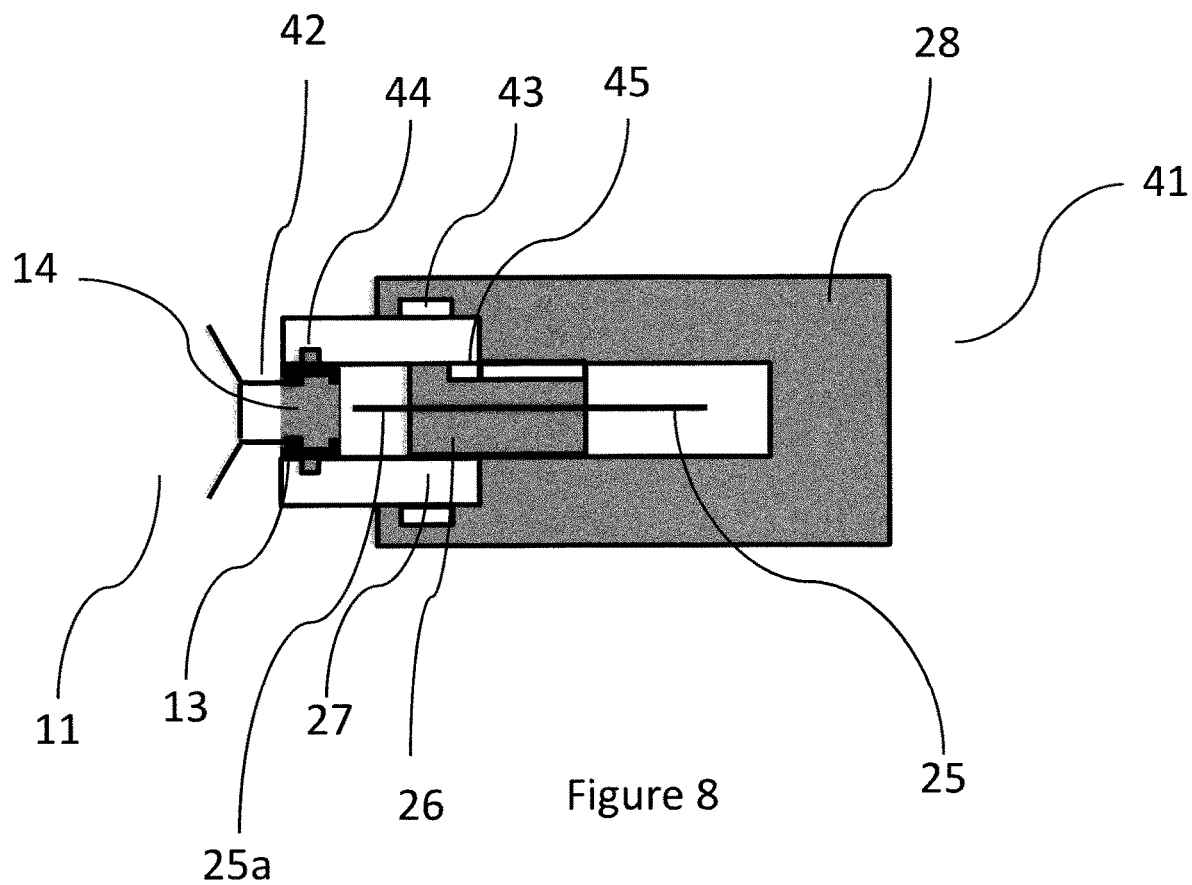
FIG. 8 is a schematic illustration showing details of a valve and needle assembly for use in forming an auto-injector assembly according to an embodiment of the invention.

In FIG. 8 details of the needle assembly 41 are shown in more detail. A valve housing 27 is sealingly mounted onto a cartridge ferrule 13 and sealed with a soft elastomeric ring 44 to keep the inner parts of the valve assembly 41 sterile including the hollow needle 25a and the hypodermic needle 25. A shuttle 26 is mounted within the housing 27 and allowed to move freely within. The shuttle is prevented from excess outwards movement by a lug 45. A needle cap 28 keeps the hypodermic needle 25 and the hollow needle 25a sterile prior to use. The needle cap 28 may be made of a soft elastomeric or a hard plastic, in which case an elastomeric ring 43 can be used to keep the inner parts of the needle assembly 41 sterile prior to use.

The needle cap 28 is not in contact with the Needle 25, unlike the situation in conventional auto-injector assemblies where the needle is impaled into the cap or boot to prevent evaporation from the needle. In the present invention the needle is dry during storage so that the needle needn't be impaled into the cap. This has the advantage that smaller hypodermic needles 25 can be used with the present invention without being damaged by the cap 28. For example gauge 29, 30 and 31 may be used. This is not generally possible with conventional staked needle devices as the needle needs to be closed by a boot which can cause needle damaged.

Figure 9:
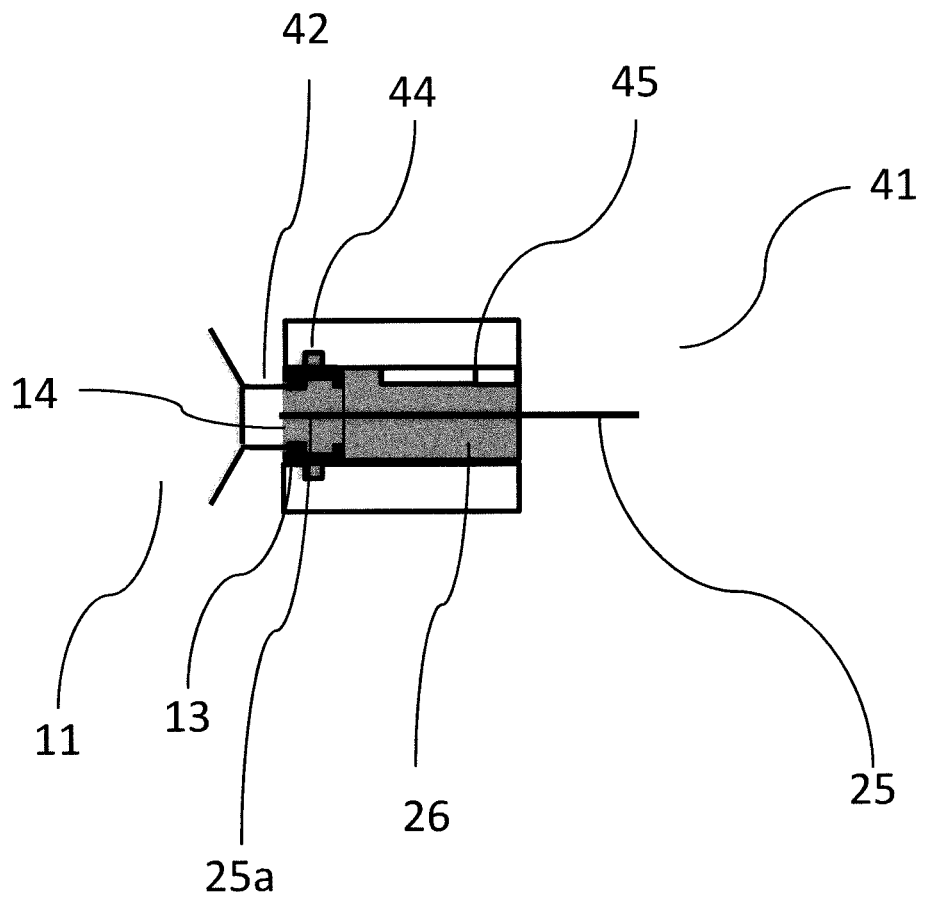
FIG. 9 is a schematic illustration showing details of a valve and needle assembly for use in forming an auto-injector assembly according to an embodiment of the invention.

In FIG. 9 the needle assembly 41 is shown during and after the injection takes place. The cap 28 has been removed. The shuttle 26 has been pushed towards the cartridge 11 and the hollow needle 25a has pierced the septum 14 allowing the pressurised drug within the cartridge 11 to flow out via needles 25a and 25 into the patient.

Figure 10:
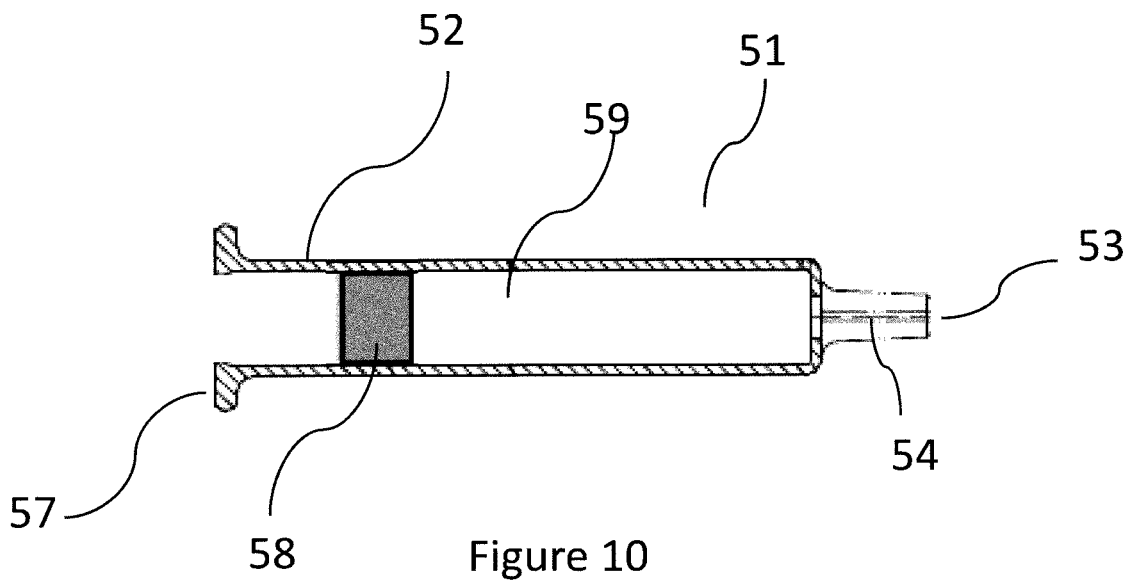
FIG. 10 is a schematic illustration of a standard pre-filled syringe as typically used in the pharmaceutical industry, and suitable for use as a medicament container in an auto-injector assembly according to an embodiment of the invention.

In FIG. 10 a conventional state of the art ready to fill syringe 51 is shown as an alternative Primary Pack for an auto-injector assembly. A syringe barrel 52 has at one end a flange 57 and at the other a Luer cone 53 defining a passageway 54. A piston or stopper 58 is located within the syringe barrel 52, which holds the liquid medicament contents 59.

Figure 11:
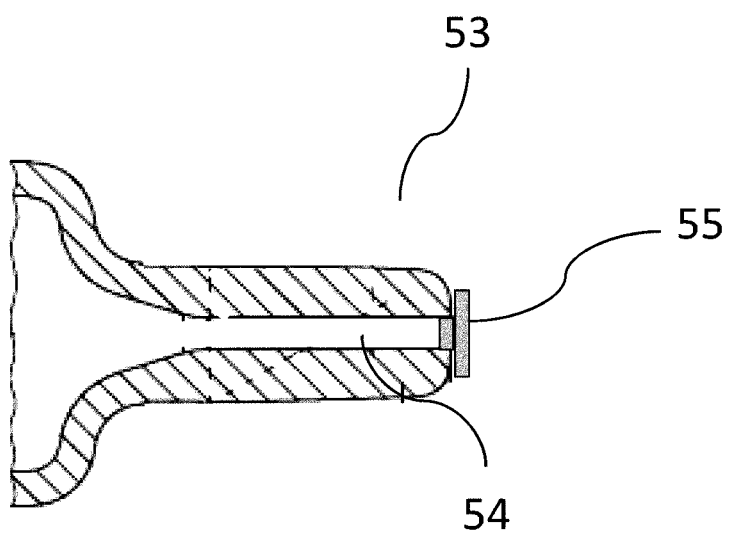
FIG. 11 illustrates a septum closure for a pre-filled syringe.

In FIG. 11 the cone 53 is shown with a septum 55 sealingly mounted on the cone 53, thereby closing the passageway 54. The seal or septum 55 may be held into place by a Luer lock system (not shown), which may include a needle/shuttle arrangement as described earlier.

Figure 12A:
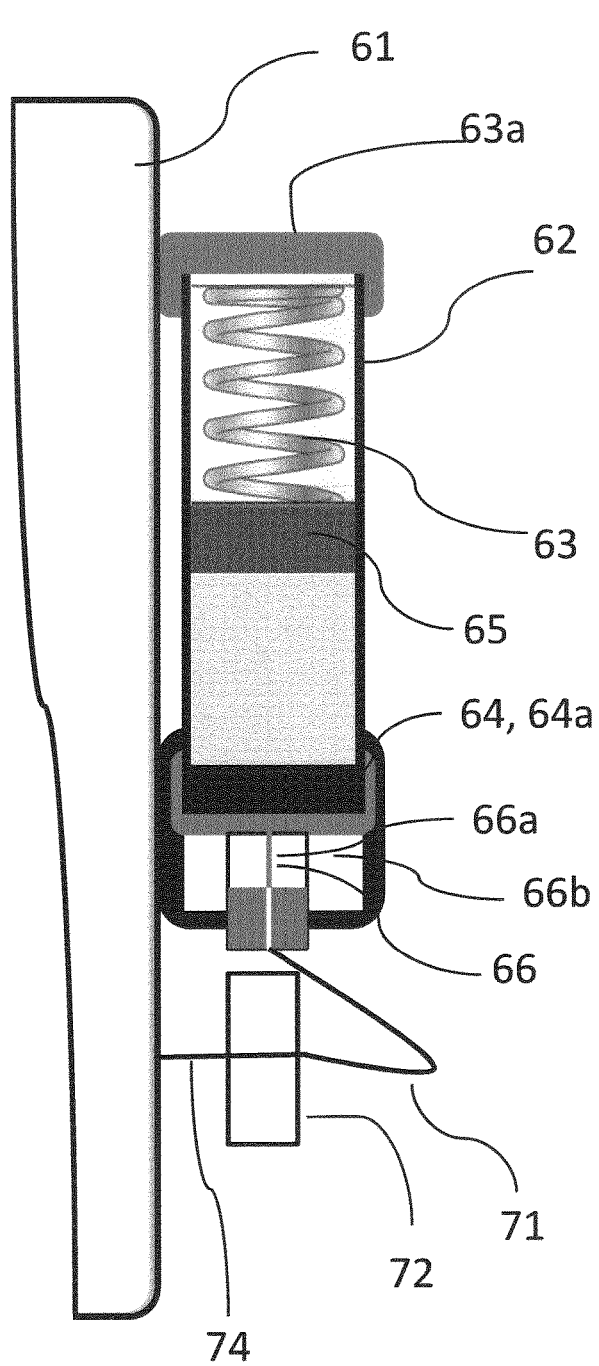

In FIGS. 12a to 12d a further embodiment of an auto-injector assembly is shown, in this case as a large volume injector. In FIG. 12a the injector is shown before use, in FIG. 12b after inserting the needle into the patient, in FIG. 12c after opening the valve, and in FIG. 12d during injection.

A standard cartridge is made up of a cartridge barrel 62, a stopper 65, a septum 64 and a ferrule 64a. The cartridge contains a liquid drug solution or suspension 67. Such cartridges are typically used in pen injectors and the like.

A spring 63 is held in place by a cap 63a. The solution 67 is pressurised by the action of the spring against the stopper. A needle 66 is held in a shuttle 66a which is allowed to move within a cap 66b. The needle 66 is connected to a flexible tube 71, which is connected to an injection needle 74 located by a pad 72. The whole assembly is attached to an injection site 61.

Figure 12B:
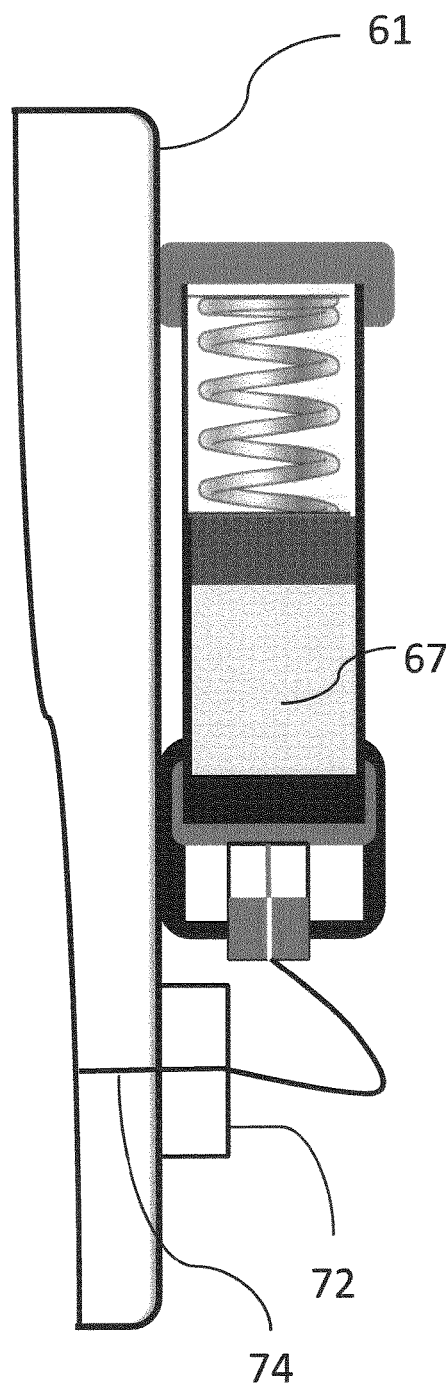

The first step is shown in FIG. 12b, in which the injection needle 74 is pushed into injection site 61 by pushing on the pad 72. The pad determines the depth of penetration of the needle 74.

The second step is shown on FIG. 12c where the needle 66 is pushed through the septum 64 communicating with the pressurised drug 67 by pushing the shuttle 66a towards the septum 64. The drug 67 is then forced into the injection site 61 via the hollow needle 66, the flexible tube 27, and the injection needle 74.

In FIG. 12d the injection is taking place and the stopper 65 has pushed out all some of the drug 67 into the delivery site 61 as a bolus 61a.

The invention claimed is:

1. An auto-injector assembly comprising:
   a medicament container defining a substantially cylindrical chamber containing a liquid medicament, a proximal end of the chamber being closed by a piston slidably located within the cylindrical chamber, and a distal end of the chamber being closed by a container seal spanning an opening at a distal end of the medicament container, wherein the container seal is a pierceable septum;
   biasing means coupled to the piston and acting to bias the piston towards the container seal, thereby pressurizing the liquid medicament;
   a hypodermic needle for parenteral administration of the liquid medicament;
   a removable needle cap for maintaining the hypodermic needle in sterile conditions until use; and
   means for establishing fluid communication between the chamber and the hypodermic needle such that the pressurized liquid medicament is automatically delivered through the hypodermic needle when the fluid communication has been established;
   wherein the means for establishing fluid communication is a valve comprising a valve housing defining a bore, wherein the valve housing is coupled to the distal end of the container such that the pierceable septum is located at a proximal end of the bore, and a shuttle is slidably retained within the bore, the shuttle comprising a piercing element for piercing the pierceable septum when the shuttle is moved towards the proximal end of the bore to establish the fluid communication between the chamber and the hypodermic needle; and
   wherein the liquid medicament is stored under positive pressure relative to atmosphere at all times during its shelf life.

2. The auto-injector assembly according to claim 1 in which the piercing element is a hollow needle extending from a proximal surface of the shuttle and is disposed in fluid communication with the hypodermic needle.

3. The auto-injector assembly according to claim 2 in which the hypodermic needle extends from a distal surface of the shuttle.

4. The auto-injector assembly according to claim 1 in which the piercing element and the hypodermic needle are formed by opposite ends of a double-ended needle located by the shuttle.

5. The auto-injector according to claim 1 in which the valve housing is sealingly coupled to the container such that the piercing element is maintained in sterile conditions until use.

6. The auto-injector assembly according to claim 5 in which the container seal is a polymeric septum coupled to the opening at the distal end of the medicament container by a metal crimp, and the valve housing is sealingly coupled to an external radial surface of the metal crimp.

7. The auto-injector assembly according to claim 1 in which the medicament container is one of a standard pre-filled cartridge or pre-filled syringe, the container seal being an elastomeric seal affixed by a metal crimp.

8. The auto-injector assembly according to claim 1 in which the container seal comprises an elastomeric septum spanning the opening at the distal end of the container, the elastomeric septum defining a through-hole sealed by a proximal end of a slidable valve stem retained by the elastomeric septum, the valve stem defining a valve stem channel in communication with the hypodermic needle, and wherein the means for establishing fluid communication is a valve comprising a valve housing defining a bore, the valve housing coupled to the distal end of the container such that the elastomeric septum is located at a proximal end of the bore, and a shuttle slidably retained within the bore, the shuttle locating the valve stem such that, when the shuttle is moved towards a proximal end of the bore, a cross-hole defined in the valve stem allows liquid to pass into the valve stem channel to establish fluid communication between the chamber and the hypodermic needle.

9. The auto-injector assembly according to claim 1 in which the piston is coupled to a spring for biasing the piston towards the container seal.

10. The auto-injector assembly according to claim 9 further comprising a cap for sealing a proximal end of the medicament container, the spring being retained between the cap and the piston to exert a force urging the piston towards the container seal.

11. The auto-injector according to claim 10 in which the cap seals the chamber of the medicament container against one or more of oxygen and humidity.

12. The auto-injector assembly according to claim 9 further comprising a casing, the casing engaging with a proximal portion of the medicament container, the spring being retained between a portion of the casing and the piston to exert a force urging the piston towards the container seal.

13. The auto-injector assembly according to claim 12 in which the casing seals the chamber of the medicament container against one or more of oxygen and humidity.

14. The auto-injector assembly according to claim 12 in which the casing comprises windows for viewing the medicament container.

15. The auto-injector assembly according to claim 1 in which the means for establishing fluid communication between the chamber and the hypodermic needle comprises a length of flexible tubing.

16. The auto-injector assembly according to claim 1 in which the removable needle cap is located out of contact with the hypodermic needle.

17. A method of producing an auto-injector assembly, comprising the steps of:
    filling a medicament container with a liquid medicament and sealing the liquid medicament within the container by applying a container seal to a distal opening of the container, wherein the container seal is a pierceable septum, the liquid medicament being retained within the medicament container under positive pressure relative to atmosphere at all times during its shelf life;
    coupling a hypodermic needle to the container via a means for establishing fluid communication between the liquid medicament and the hypodermic needle, the means being a valve comprising a valve housing defining a bore, wherein the valve housing is coupled to a distal end of the container such that the pierceable septum is located at a proximal end of the bore, and a shuttle is slidably retained within the bore, the shuttle comprising a piercing element for piercing the pierceable septum when the shuttle is moved towards the proximal end of the bore to establish fluid communication between the container and the hypodermic needle;
    protecting the hypodermic needle with a removable needle cap for maintaining the hypodermic needle in sterile conditions until use, the needle cap not being in contact with the needle; and
    sealing the valve housing to the container such that the piercing element is maintained in sterile conditions until use;
    wherein the filling, coupling, protecting, and sealing steps are carried out in a sterile environment.

18. The auto-injector assembly according to claim 1 wherein the positive pressure relative to atmosphere under which the liquid medicament is stored minimizes likelihood of foreign matter entering and compromising the sterile conditions and contaminating the liquid medicament.

19. The method according to claim 17 wherein the pressurized liquid medicament is automatically delivered through the hypodermic needle when the fluid communication has been established.

20. The method according to claim 17 wherein retaining the liquid medicament under positive pressure relative to atmosphere minimizes likelihood of foreign matter entering and compromising the sterile conditions and contaminating the liquid medicament.

* * * * *